United States Patent [19]

Christensen et al.

[11] 4,298,741
[45] Nov. 3, 1981

[54] 6-AMIDO-3-SUBSTITUTED-1-AZABICY-CLO[3.2.0]-HEPT-2-EN-7-ONE-2-CARBOXYLIC ACID

[75] Inventors: Burton G. Christensen, Metuchen; Ravindra N. Guthikonda, Perth Amboy; Ronald W. Ratcliffe, Matawan, all of N.J.

[73] Assignee: Merck & Co., Inc., Rahway, N.J.

[21] Appl. No.: 168,947

[22] Filed: Jul. 11, 1980

Related U.S. Application Data

[63] Continuation of Ser. No. 927,319, Jul. 24, 1978, abandoned.

[51] Int. Cl.³ .............. C07D 487/04; C07D 205/08; A61K 31/40; C07D 409/12
[52] U.S. Cl. .................. 546/272; 260/239 A; 260/245.2 T; 544/355; 424/250; 424/263; 424/274
[58] Field of Search ............. 260/245.2 T; 546/272; 544/355

[56] References Cited
U.S. PATENT DOCUMENTS
4,218,463 8/1980 Christensen et al. ........... 260/239 A Primary Examiner—Mark L. Berch
Attorney, Agent, or Firm—Hesna J. Pfeiffer; James A. Arno; Julian S. Levitt

[57] ABSTRACT

Disclosed are 6-amido-3-substituted-1-azabicyclo[3.2.0]hept-2-en-7-one-2-carboxylic acids (I):

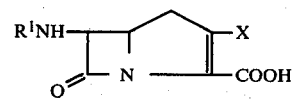

wherein
  $R^1$ is hydrogen or acyl; and
  X is halo, oxygen (the 2–3 bond is saturated and the species I exists as a carboxylate salt or ester), or —OR wherein R is, inter alia, acyl, alkyl, or aralkyl. Such compounds and their pharmaceutically acceptable salt, ester and amide derivatives are useful as antibiotics. Also disclosed are processes for the preparation of such compounds, pharmaceutical compositions comprising such compounds and methods of treatment comprising administering such compounds and compositions when an antibiotic effect is indicated.

2 Claims, No Drawings

6-AMIDO-3-SUBSTITUTED-1-AZABICYCLO[3.2.0]-HEPT-2-EN-7-ONE-2-CARBOXYLIC ACID

This is a continuation of application Ser. No. 927,319, filed July 24, 1978, now abandoned.

BACKGROUND OF THE INVENTION

This invention relates to 6-amido-3-substituted-1-azabicyclo[3.2.0]hept-2-en-7-one-2-carboxylic acids and their pharmaceutically acceptable salt, ester and amide derivatives (I) which are useful as antibiotics:

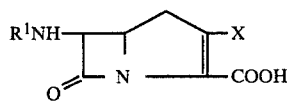

wherein $R^1$ is hydrogen or an acyl radical known to be effective in the related bicyclic β-lactam antibiotic art such as the penicillins and cephalosporins, X is halo such as chloro or bromo, oxygen (the 2-3 bond is saturated and the species I exists as a carboxylate salt or ester), or —OR wherein R is, inter alia, acyl, alkyl, or aralkyl. The radicals $R^1$ and X are more fully defined below. It will be recognized that when X is oxygen, the species I exhibits enol-keto tautomerism wherein the substituent X may also assume the value of —OH.

This invention also relates to carboxylate derivatives of I which are also antibiotics and which may be represented by the following generic structure:

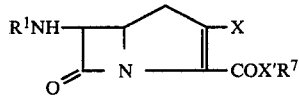

wherein X' is oxygen, sulphur or NR' (R'=H or loweralkyl having 1-6 carbon atoms); and $R^7$ is, inter alia, representatively selected from the group consisting of hydrogen, conventional blocking groups such as trialkylsilyl, acyl and the pharmaceutically acceptable salt, ester and amide moieties known in the bicyclic β-lactam antibiotic art; the definition of $R^7$ is given in greater detail below.

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyogenes* and *B. subtilis,* and gram negative bacteria such as *E. coli, Proteus morganii,* Pseudomonas, Serratia and Klebsiella. Further objects of this invention are to provide chemical processes for the preparation of such antibiotics and their non-toxic pharmaceutically acceptable salts; pharmaceutical compositions comprising such antibiotics and to provide methods of treatment comprising such antibiotics and compositions when an antibiotic effect is indicated.

DETAILED DESCRIPTION OF THE INVENTION

The preparation of the compounds (I) of the present invention may conveniently be summarized by the following reaction diagram:

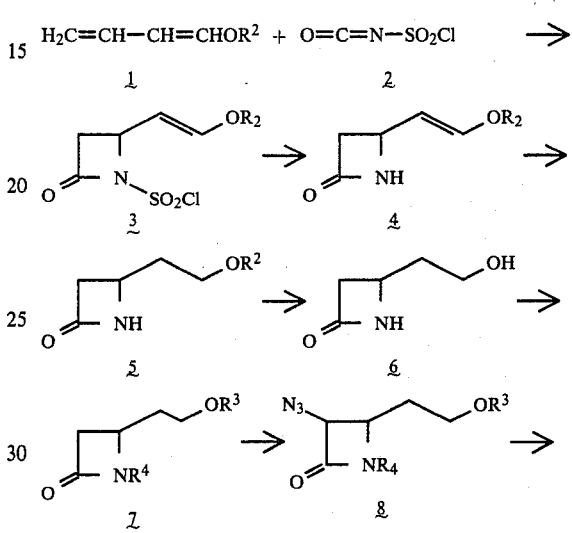

In words relative to the above diagram, the 4-(2-substituted-vinyl)azetidine-2-one, 4, starting material is prepared by reacting an $R^2$-oxybutadiene, 1, with chlorosulfonylisocyanate 2. The reaction is conducted without solvent or may be run in solvent such as diethyl ether, ethyl acetate, chloroform, methylene chloride, or the like at a temperature of from −78° C. to 25° C. for from a few minutes to 1 hour to provide 3. The radical $R^2$ is an easily removable acyl blocking group such as an alkanoyl or aralkanoyl which bears no functional group or groups which might interfere with the desired course of reaction (1+2→3→4). Intermediate species 3 is converted to the sulfinamide by reductive hydrolysis to 4 at pH 6-8. Typically the reaction solution comprising 3 is connected (5-30 minutes) with an aqueous solution (at 0°-25° C.) of a reducing agent such as sodium sulfite, thiophenol, or the like, at pH 6-8 to provide 4.

The reaction 4→5 is a reduction, and is preferably achieved by hydrogenation in a solvent such as ethyl acetate, ether, dioxane, tetrahydrofuran (THF), ethanol or the like at 0° to 25° C. for from 5 minutes to 2 hours under 1 to 10 atmospheres of hydrogen in the presence of a hydrogenation catalyst such as a platinum metal or oxide thereof such as 10% Pd/C or the like.

The de-blocking reaction 5→6 is usually desirable when $R^2$ is acyl to permit the establishment of preferred protecting groups $R^3$ and $R^4$. The preferred deblocking procedure is by alcoholysis wherein the solvent is a lower alkanol such as methanol, ethanol or the like in the presence of the corresponding alkali metal alkoxide, such as sodium methoxide. Typically, the reaction is conducted for from 5 minutes to 1 hour at a temperature of from −10° to 25° C.

Blocking groups $R^3$ and $R^4$ are established ($\underline{6}\rightarrow\underline{7}$) to provide a suitably protected species for introduction of the azide ($\underline{7}\rightarrow\underline{8}$). There is no criticality in the choice of blocking groups, provided only that they do not interfere with the intended reaction. $R^4$ may be hydrogen, a triorganosilyl group, such as trimethylsilyl or the like, or a cyclic ether such as 2-tetrahydropyranyl; $R^3$ may also be a cyclic ether such as 2-tetrahydropyranyl; alternatively $R^3$ and $R^4$ may be joined together to form protected species such as $\underline{7}$a:

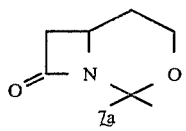

For example, a species such as $\underline{7}$a is conveniently prepared by treating $\underline{6}$ with 2,2-dimethoxypropane in the presence of a catalyst such as boron trifluoride etherate, toluene sulphonic acid, or the like in a solvent such as methylene chloride, ether, chloroform, dioxane or the like at a temperature of from $-10°$ to $35°$ C. for from a few minutes to 1 hour.

The azide intermediate $\underline{8}$ is prepared by treating $\underline{7}$ in a solvent such as tetrahydrofuran (THF), dimethoxyethane, ether or the like with a base such as lithium diisopropylamide, n-butyl lithium, potassium hydride or the like at a temperature of from $-78°$ to $0°$ C. for from 2 to 60 minutes; whereupon an azide reagent such as tosylazide is introduced; after 0.5 to 5 hours at $-78°$ to $0°$ C., the mixture is treated with a disproportionating agent such as trimethylchlorosilane to provide the azide $\underline{8}$ which may be isolated and resolved into its cis and trans isomers by conventional chromatographic techniques.

The following diagram illustrates a particularly preferred scheme for proceeding from intermediate species $\underline{8}$, above:

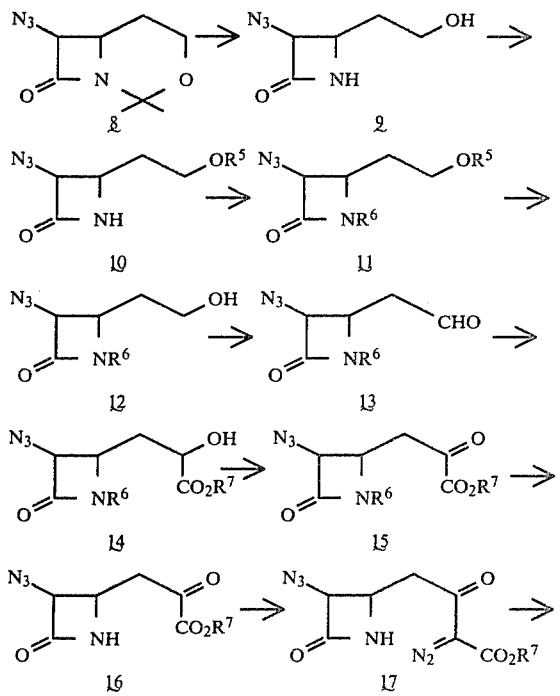

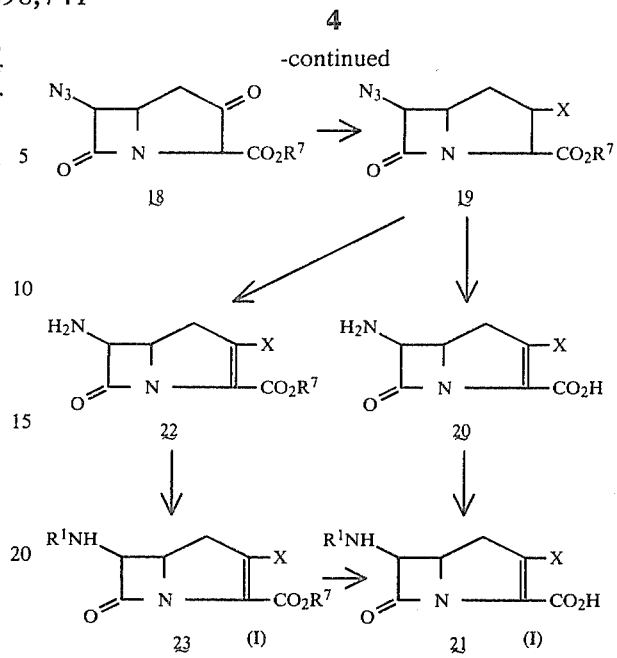

The deblocking reaction $\underline{8}\rightarrow\underline{9}$ is typically conducted by acid hydrolysis such as aqueous trifluoroacetic acid at a temperature of from $0°-25°$ C. for from 5 minutes to 3 hours.

The reaction $\underline{9}\rightarrow\underline{10}$ is an O-acylation wherein the radical $R^5$ is an easily removable acyl blocking group such as an alkanoyl or aralkanoyl which bears no functional group or groups which might interfere with the desired course of reaction detailed herein. Conventional O-acylation techniques may be employed to establish $R^5$. When the acylating agent is an acyl halide such as acetyl chloride, benzoyl chloride or the like, the substrate $\underline{9}$ in a solvent such as methylene chloride, ether, tetrahydrofuran or the like in the presence of triethylamine, pyridine, or the like is treated with the acyl halide to form $\underline{10}$. When an acid anhydride reagent is employed to establish $R^5$ suitable reaction solvents include methylene chloride, ether, benzene or the like in the presence of triethylamine, pyridine, or the like; wherein the reaction is conducted at a temperature range of from $-20°$ to $50°$ C. for from 10 to 120 minutes. Suitable anhydrides include trifluoroacetic anhydride, acetic anhydride, benzoic anhydride and the like.

The reaction $\underline{10}\rightarrow\underline{11}$ establishes the N-protecting group $R^6$ which preferably is a triorganosilyl radical such as trimethylsilyl or t-butyldimethylsilyl. Such triorganosilyl radicals are established by treating $\underline{10}$ in a solvent such as dimethylformamide (DMF), dioxane, tetrahydrofuran (THF) diethylether or the like in the presence of a base such as triethylamine, imidazole, pyridine or the like with the desired silylating agent such as t-butyldimethylsilylchloride, propyldimethylsilylchloride or the like at a temperature of from $-10°$ to $40°$ C. for from 10 minutes to 8 hours.

The deblocking reaction $\underline{11}\rightarrow\underline{12}$ is preferably accomplished by alcoholysis wherein the solvent is a loweralkanol such as methyl or the like in the presence of the corresponding alkali metal alkoxide such as sodium methoxide. Typically the reaction is conducted for from 5 minutes to 3 hours at a temperature of $-10°$ to $25°$ C.

The aldehyde intermediate $\underline{13}$ is prepared by treating $\underline{12}$ with an oxidizing agent such as $CrO_3.2$ (pyridine) in $CH_2Cl_2$; 1:1 mixture of dimethylsulfoxide (DMSO) and acetic anhydride; pyridinium chlorochromate in $CH_2Cl_2$; dicyclohexacarbodiimide in DMSO, methylene chloride or the like at a temperature of from 0°–25° C. for from 5 minutes to 8 hours.

The condensation of the aldehyde 13 to provide species 14 is accomplished by treating 13 in a solvent such as diethylether, THF, TMF, hexamethylphosphoramide (HMPA) or the like at a temperature of from −78° C. to 0° C. for from 1 minute to 1 hour in the presence of a base such as lithium diisopropylamide, potassium hydride, or the like with an ester of acetic acid: $CH_3CO_2R_7$ wherein $R_7$ is a readily removable carboxyl protecting group or a pharmaceutically acceptable ester moiety. Preferred protecting groups include t-butyl, benzyl, p-methoxybenzyl, antracenylmethyl, or the like; whereas preferred pharmaceutically acceptable ester moieties include 3-methyl-2-butenyl, p-t-butylbenzyl, p-phenoxybenzyl, or the like.

Intermediate ketone species 15 is obtained by oxidation of 14 following the previously described oxidation procedure for 12→13.

The deblocking reaction 15→16 is accomplished by mild acid hydrolysis such as acetic or hydrochloric acid in methanol at a temperature of from 15°–50° C. for from 1–20 hours.

The diazo transfer reaction 16→17 is accomplished by treating 16 in a solvent such as $CH_3CN$, $CH_2Cl_2$, THF, or the like with an azide such as p-carboxybenzenesulfonyl azide, toluene sulfonyl azide, methane sulfonyl azide or the like in the presence of base such as triethylamine, pyridine, diethylamine or the like at a temperature of from 0°–25° C. for from 1 to 50 hours.

Cyclization of the diazo compound to provide 18 (17→18) is preferably accomplished by irradiating through a pyrex filter (wave length greater than 300 nm) in a solvent such as benzene, $CCl_4$, $Et_2O$, or the like at a temperature of from 0° to 25° C. for from 0.5 to 2 hours. Alternatively, cyclization of the diazo compound is accomplished by heating in a solvent such as benzene ($\phi H$), toluene, ($\phi Me$), THF, or the like at a temperature of from 50° to 100° C. for 1–5 hours in the presence of a catalyst such as bis (acetylacetonato)Cu(II), [Cu(acac)$_2$], $CuSO_4$, $Cu°$ powder, $Rh_2(OAc)_4$, or $Pd(OAc)_2$.

The 3-keto species 18 serves as a common intermediate for the preparation of 3-halo(X=Cl, Br), ester (X=OR and R=acyl) and ether (X=OR and R is inter alia, aralkyl or alkyl) embodiments of the present invention. The preferred values of R (as well as $R^1$ and $R^7$, see Structure I, above) are given below.

Embodiments of the present invention (I) wherein R is acyl are prepared by reacting species 18 in a solvent such as benzene, $CH_2Cl_2$, THF, DMF or the like in the presence of a base such as $Et_3N$, pyridine, 4-dimethylaminopyridine, propylene oxide or the like at a temperature of from 0°–25° with a reagent calculated to introduce the acyl radical of choice. Generically, such acylating reagents may be selected from the following list of reagents, acid chlorides: RCOCl, $RSO_2Cl$, $R_2POCl$; acid anhydrides: $(RCO)_2O$, $(RSO_2)_2O$; ketene; activated acid esters and the like. Representative examples of such reagents are:

ketene,
acetic anhydride,
acetyl chloride,
azido acetyl chloride,
phenylacetyl chloride,
benzoic anhydride,
benzoyl chloride,
propionic anhydride,
diphenyl ketene,
p-nitrophenyl chloroacetate,
N-benzyloxycarbonyl glycyl chloride,
methanesulfonyl chloride,
p-toluenesulfonic anhydride,
p-toluenesuflonyl chloride.

Embodiments of the present invention (I) wherein R is other than acyl which generically may be classified as ethers are conveniently prepared from the 3-keto intermediate species 18 by treating 18 with a diazo reagent calculated to provide the radical R in a solvent such as $Et_2O$, $CH_2Cl_2$, MeOH, $\phi H$, $CH_3CN$ or the like at a temperature of from 0° to 80° C. for from 15 mins to 2 hours. Representative examples of such diazo reagents are:
diazomethane,
1-diazobutane,
3-propyl-1-p-tolyltriazene,
3-ethyl-1-p-tolyltriazene,
3-benzyl-benzyl-1-p-tolyltriazene,
phenyldiazomethane,
diphenyldiazomethane.

In addition, the ether embodiments may be obtained by alkylating the keto ester intermediate 18 with a reagent RX° in the presence of base. Suitable reagents RX° may be $CH_3SO_3F$, $(CH_3)_2SO_4$, $CF_3SO_3CH_2CH_2N_3$, or $TsOCH_2CH_2N_3$ (X° is a leaving group and Ts=tosyl); suitable solvents for the reaction include acetone, hexamethylphosphoramide (HMPA), DMF, THF, dioxane or the like in the presence of base such as potassium carbonate or potassium tertiary butoxide, sodium hydride, or the like at a temperature of from −20° to 40° C. for from 0.5 to 3 hours.

Embodiments of the present invention wherein R is halo are prepared by treating 18 with a halogenating agent such as $PCl_3$, $SOCl_2$, $POCl_3$, $(COCl)_2$, $PBr_3$, $SOBr_2$ $\phi_3PCl_2$ or the like in a solvent such as DMF, $CHCl_3$, $\phi H$ or the like for from 0.5 to 8 hours at 0° to 80° C. Preferred reagents and conditions for preparation of the 3-chloro species are $\phi_3PCl_2$, $PCl_3$ or $SOCl_2$ in a solvent such as DMF at a temperature of 0° to 25° C. for from 1 to 6 hours. Preferred reagents and conditions for preparation of the 3-bromo species are $PBr_3$ or $SOBr_2$ in a solvent such as DMF at a temperature of from 0° to 25° C. for from 1 to 6 hours.

Regardless of the identity of X, species 19 is converted to the 6-amino compound 22 by treating 19 in a solvent such as ethylacetate, dioxane, ethanol or the like in the presence of a platinum of palladium metal catalyst such as 10% palladium on carbon under hydrogen pressure of from 1–4 atmospheres for from 1–24 hours at 0°–25° C. The deblocking of the carboxyl group to provide species 20 may also be accomplished under the condition substantially as described for the transition 19→22. The N-acylation reaction 22→23 or 20→21 (I) May be accomplished by any of a variety of well known procedures (the analogous reactions in the 6-amino penicillin and 7-amido cephalosporin series are well known and are opposite here) such as treating 22 in a solvent such as methylene chloride, chloroform or the like with an acid chloride calculated to provide the acyl radical $R^1$ in the presence of from 1–5 equivalents of pyridine or triethylamine or by treating 20 in a solvent such as aqueous dioxane or acetone with an acid chloride in the presence of 1–5 equivalents of $K_2HPO_4$ or $NaHCO_3$ at a temperature of from 0°–25° C. for from 5-60 minutes. Preferred acylating agents for this purpose are representatively given below:

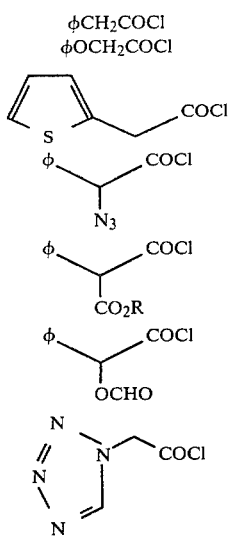

The final carboxyl deblocking reaction $\underline{23}\rightarrow\underline{21}$ may be accomplished by any of a variety of well known deblocking reactions such as hydrolysis or preferably hydrogenation in a solvent such as ethanol, aqueous dioxane, or the like in the presence of a palladium catalyst such as 10% Pd/C, PdO$_2$, or the like at a hydrogen pressure of from 1 to 4 atmospheres for from 0.5 to 2 hours at a temperature for from 0° to 25° C.

IDENTIFICATION OF THE RADICAL X

In the generic description of the compounds of the present invention (I):

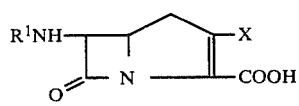

X is oxygen, halo, such as bromo or chloro, or —OR wherein R is selected from the group consisting of substituted and unsubstituted: alkyl, having 1-6 carbon atoms, cycloalkyl and cycloalkylalkyl wherein the ring moiety comprises 3-6 carbon atoms and the alkyl moiety comprises 1-4 carbon atoms, aralkyl having from 7-16 carbon atoms, and acyl; wherein the substituent or substituents on the radical R are selected from: amino, mono-, di- and trialkylamino wherein the alkyl has 1-6 carbon atoms, chloro, bromo, amidino, guanidino, and carboxyl. Generically, the term "acyl" as it relates to the definition of R is inclusive of the alkanoyls including derivatives and analogues thereof such as thio analogues wherein the carboxyl oxygen is replaced by sulphur; as well as sulphur and phosphorous acyl analogues such as substituted sulfonyl-, sulfinyl-, and sulfenyl-radicals, and substituted p (III and V) radicals such as substituted phosphorous-, phosphoric-, phosphonous- and phosphonic-radicals, respectively. Such acyl radicals of the present invention are further defined below.

Representative of such acyl radicals, R, are:

wherein X is O or S and R' (or R") is OR", NR$_2$", SR", substituted or unsubstituted alkyl having 1-6 carbon atoms, aryl such as phenyl, aralkyl such as benzyl or phenethyl, or heterocycle wherein the hetero atom or atoms are selected from oxygen, sulfur, and nitrogen. More specifically suitable acyl radicals, R, are:

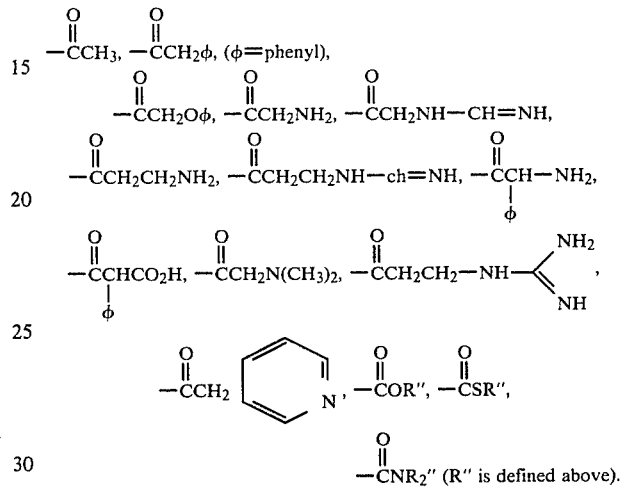

The radical R may also be

wherein R' is as defined above;

wherein R' is as defined above; and

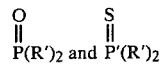

wherein R' is —OR" or —NR$_2$".

Relative to the definition of the compounds of the present invention (I) the most preferred values for the radical R are those selected from the group consisting of lower alkyl having from 1-6 carbon atoms such as methyl, ethyl, propyl and the like, aralkyl such as benzyl, diphenylmethyl and the like. Substituted alkyl such as 2-aminoethyl, 3-aminopropyl, 2-formamidoylaminoethyl and the like and substituted aralkyl such as p-carboxybenzyl, p-aminobenzyl, p-hydroxybenzyl, pyridylmethyl, and the like; and

wherein R' is selected from the above-defined unsubstituted or substituted: alkyl, aralkyl, aryl for example:

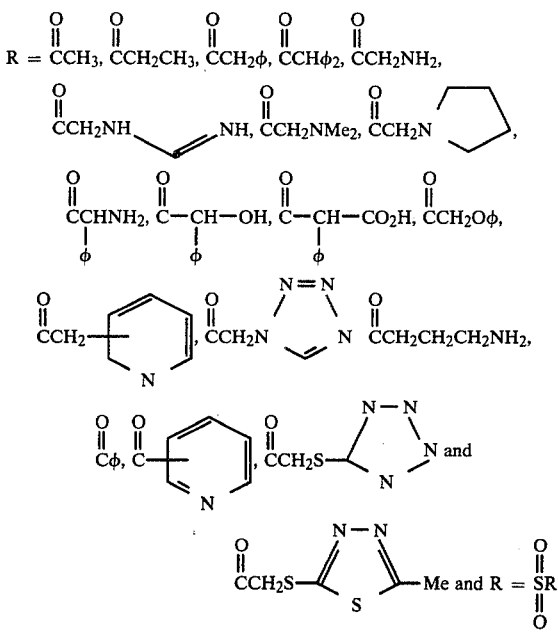

wherein R' is selected from the above-identified unsubstituted or substituted: alkyl, or aryl, for example:

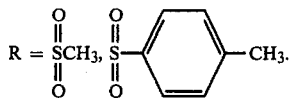

Identification of the Acyl Radical $R^1$ of Structure I

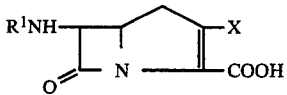

In the generic representation of the compounds of the present invention (I, above), the acyl radical represented by $R^1$ can, inter alia, be substituted or unsubstituted: aliphatic, aromatic or heterocyclic, araliphatic or heterocyclyaliphatic carboxylic acid radical, a substituted or unsubstituted: carbamyl radical or a carbothioic acid radical. One group of acyl radicals can be represented by the general formula:

wherein X is O or S and R" represents hydrogen; amino; substituted amino such as alkyl- and dialkylamino wherein the alkyl radical comprises 1 to about 6 carbon atoms; substituted or unsubstituted; straight or branched chain alkyl wherein the alkyl radical comprises 1 to about 6 carbon atoms; mercapto such as alkylthio, typically comprising 1 to 6 carbon atoms; arylthio, typically comprising 6 to 10 carbon atoms; hydroxy such as alkoxy, typically comprising 1 to 6 carbon atoms; aryloxy, typically comprising 6 to 10 carbon atoms; alkenyl, or alkynyl groups typically comprising 2 to 6 carbon atoms; aryl such as phenyl; aralkyl such as benzyl; cycloalkyl, typically comprising 3 to 6 carbon atoms; or a heteroaryl or heteroaralkyl group (mono- and bicyclic) wherein the alkyl moiety typically comprises 1 to 3 carbon atoms and the heterocyclic ring comprises typically 4–10 atoms and the hetero atom or atoms are selected from O, N and S; such above-listed groups can be unsubstituted or can be substituted by radicals such as OH, SH, SR° (R° is lower alkyl or aryl such as phenyl), alkyl or alkoxy groups having 1 to about 6 carbon atoms, halo such as Cl, Br, F and I, cyano, carboxy, sulfamino, carbamoyl, sulfonyl, azido, amino, substituted amino such as alkylamino including quaternary ammonium wherein the alkyl group comprises 1 to 6 carbon atoms, haloalkyl such as trifluoromethyl, carboxyalkyl, carbamoylalkyl, N-substituted carbamoylalkyl, wherein the alkyl moiety of the foregoing four radicals comprises 1 to about 6 carbon atoms, amidino, guanidino, N-substituted guanidino, guanidino lower alkyl and the like. Representative examples of such acyl groups that might be mentioned are those wherein R" is benzyl, p-hydroxybenzyl, 4-amino-4-carboxybutyl, methyl, cyanomethyl, 2-pentenyl, n-amyl, n-heptyl, ethyl 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4-N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)-4-isoxazolyl, 4-guanidinomethylphenyl, 4-guanidinomethylbenzyl, 4-guanidinobenzyl, 4-guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl)vinyl, phenyl, o-methoxyphenyl, o-chlorophenyl, 1-phenylphenyl, p-aminomethylbenzyl, 1-(5-cyanotriazolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl)methyl, 2- or 3-(methoxythienyl)methyl, 2- or 3-(4-chlorothienyl)methyl, 2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, tetrazolylmethyl benzamidinomethyl and cyclohexylamidinomethyl.

The acyl group can also be a radical of the formula:

wherein X is O or S and n is 0–4, Z represents oxygen, sulfur, carbonyl or nitrogen and R" is defined as above. Representative members of the substituent —(CH$_2$)$_n$ZR'' that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)phenylthiomethyl, 2-thiazolylthiomethyl, p-(sulfo)phenoxymethyl, p-(carboxymethyl)phenylthiomethyl, 2-pyrimidinylthiomethyl, phenethylthiomethyl, 1-(5,6,7,8,-tetrahydronaphthyl)oxomethyl, N-methyl-4-pyridylthio, benzyloxy, methoxy, ethoxy, phenoxy, phenylthio, amino, methylamino, dimethylamino, pyridinium methyl, trimethylammoniummethyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl and 1-pyrrolobutyl.

Alternatively, the acyl group can be a radical of the formula:

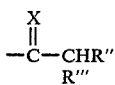

wherein R'' is defined as above and R''' is a radical such as amino, hydroxy, azido, carbamoyl, guanidino, amidino, acyloxy, halo, such as Cl, F, Br, I, sulfamino, tetrazolyl, sulfo, carboxy, carbalkoxy, phosphono and the like. Representative members of the substituent:

that might be mentioned are α-aminobenzyl, α-amino-(2-thienyl)methyl, α-(methylamino)benzyl, α-aminomethylmercaptopropyl, α-amino-3- or 4-chlorobenzyl, α-amino-3- or 4-hydroxybenzyl, α-amino-2,4-dichlorobenzyl, α-amino-3,4-dichlorobenzyl, D(—)-α-hydroxybenzyl, α-carboxybenzyl, α-amino-(3-thienyl)-methyl D-(—)-α-amino-3-chloro-4-hydroxybenzyl, α-amino(-cyclohexyl)methyl, α-(5-tetrazolyl)-benzyl, 2-thienylcarboxymethyl, 3-thienyl-carboxymethyl, 2-furylcarboxymethyl, 3-furyl-carboxymethyl, α-sulfaminobenzyl, 3-thienyl-sulfaminomethyl, α-(N-methylsulfamino)-benzyl, D(—)-2-thienyl-guanidinomethyl, D(—)-α-guanidinobenzyl, α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-sulfadiazolyl)-hydroxymethyl, 4-(5-chlorothienyl)aminomethyl, 2-(5-chlorothienyl)-hydroxymethyl, 2-(5-chlorothienyl)-carboxy-methyl, 3-(1,2-thiazolyl)-aminomethyl, 3-(1,2-thiazolyl)-hydroxymethyl, 3-(1,2-thiazolyl)carboxymethyl, 2-(1,4-thiazolyl)aminomethyl, 2-(1,4-thiazolyl)-hydroxymethyl, 2-(1,4-thiazolyl)carboxymethyl, 2-benzothienylaminomethyl, 2-benzothienylhydroxymethyl, 2-benzothienylcarboxymethyl, α-sulfobenzyl, α-phosphonobenzyl, α-diethylphosphono and α-monoethylphosphono. Further acyl radicals of interest in this class when X=oxygen are:

wherein R$^3$ and R$^4$ are as defined below. R$^3$ represents hydrogen, halo, such as chloro, fluoro, bromo, iodo amino, guanidino, phosphono, hydroxy, tetrazolyl, carboxy, sulfo, or sulfamino and R$^4$ represents phenyl, substituted phenyl, a mono- or bicyclic heterocyclyl containing one or more oxygen, sulfur or nitrogen atoms in the ring, such as furyl, quinoxalyl, thienyl, quinolyl, quinazolyl, thiazolyl, isothiazolyl, tetrazolyl, oxadiazolyl, thiadiazolyl and the like substituted heterocycles, phenylthio, phenyloxy, lower alkyl of 1–6 carbon atoms, heterocyclic or substituted heterocyclic thio groups; or cyano. The substituents on the moieties, R$^3$ and R$^4$, can be halo, carboxymethyl, guanidino, guanidinomethyl, carboxyamidomethyl, aminoethyl, nitro, methoxy or methyl. When R$^3$ is selected from the group consisting of hydrogen, hydroxy, amino or carboxy and R$^4$ is selected from the group consisting of phenyl, or a 5- or 6-membered heterocyclic ring having one or two sulfur, oxygen or nitrogen hetero atom such as tetrazolyl, thienyl, furyl and phenyl, the following acyl radicals are representative: phenylacetyl, 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl, 3-furylacetyl, 2-thienylacetyl, 5-chloro-2-thienylacetyl, 5-methoxy-2-thienylacetyl, α-guanidino-2-thienylacetyl, 3-thienylacetyl, 2-(4-methylthienyl)-acetyl, 3-isothiazolylacetyl, 4-methoxy-3-isothiazolylacetyl, 4-isothiazolylacetyl, 3-methyl-4-isothiazolylacetyl, 5-isothiazolylacetyl, 3-chloro-5-isothiazolylacetyl, 3-methyl-1,2,5-oxadiazolylacetyl, 1,2,5-thiadiazolyl-4-acetyl, 3-methyl-1,2,5-thiadiazolylacetyl, 3-chloro-1,2,5-thiadiazolylacetyl, 3-methoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-amino cyclohexadienylacetyl, α-sulfaminophenylacetyl, α-hydroxyphenylacetyl, α-tetrazolylphenylacetyl and α-sulfophenylacetyl.

R$^1$ of Structure I may also be a readily removable protecting group; a particularly preferred acyl for this purpose is o or p-nitrobenzyloxycarbonyl.

Identification of the Radical —COX'R$^7$

The generic representation of the compounds of the present invention (I) also includes structures:

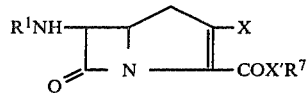

wherein: the radical represented by —COX'R$^7$ is, inter alia, —COOH (X' is oxygen and R$^7$ is hydrogen) and all radicals known to be effective as pharmaceutically acceptable ester, anhydride (X' is oxygen and R$^7$ is acyl) and amide radicals in the bicyclic β-lactam antibiotic art, such as the cephalosporins and penicillins and the nuclear analogues thereof.

Suitable radicals (R$^7$) include conventional protecting or carboxyl blocking groups. The term "blocking group" as utilized herein is employed in the same manner and in accordance with the teaching of U.S. Pat. No. 3,697,515 which is incorporated herein by reference. Pharmaceutically acceptable derivatives of the present invention falling in this class are given below. Suitable blocking esters thus include those selected from the following list which is representative and not intended to be an exhaustive list of possible ester groups wherein $X'=O$ and $R^7$ is given:

(i) $R^7=CR^aR^bR^c$ wherein at least one of $R^a$, $R^b$ and $R^c$ is an electron-donor, e.g., p-methoxyphenyl. The remaining $R^a$, $R^b$ and $R^c$ groups may be hydrogen or organic substituting groups. Suitable ester groups of this type include p-methoxybenzyloxycarbonyl.

(ii) $R^7=CR^aR^bR^c$ wherein at least one of $R^a$, $R^b$ and $R^c$ is an electron-attracting group, e.g., p-nitrophenyl, trichloromethyl, and o-nitrophenyl. Suitable esters of this type include p-nitrobenzyloxycarbonyl, and 2,2,2-trichloroethoxycarbonyl.

(iii) $R^7=CR^aR^bR^c$ wherein at least two of $R^a$ $R^b$ and $R^c$ are hydrocarbon such as alkyl, e.g., methyl or ethyl, or aryl, e.g., phenyl and the remaining $R^a$, $R^b$ and $R^c$ group, if there is one, is hydrogen. Suitable esters of this type include t-butyloxycarbonyl, diphenylmethoxycarbonyl and triphenylmethoxycarbonyl.

Silyl esters, under this category of blocking groups, may conveniently be prepared from a halosilane of the formula: $R^4_3SiX'$ wherein $X'$ is a halogen such as chloro or bromo and $R^4$ is alkyl, e.g., methyl, ethyl, t-butyl.

More generally stated, pharmaceutically acceptable carboxyl derivatives of the present invention are those derived by reacting I with alcohols, acylating reagents and the like. For example, esters and amides of interest are the above-listed starting materials and final products having the —COX′R⁷ group at the 2-position; wherein $X'$ is oxygen, sulfur or $NR^1$ ($R^1$ is H or $R^7$, and $R^7$ is alkyl having 1–6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1–6 carbon atoms and the alkyl portion has 1–6 carbon atoms, such as pivaloyloxymethyl; haloalkyl wherein halo is chloro, and the alkyl portion is straight or branched having 1–6 carbon atoms e.g., 2,2,2-trichloroethyl; alkenyl having 1–4 carbon atom such as 2-propenyl, 3-butenyl, and 4-butenyl; aralkyl and lower alkoxyl and nitro-substituted aralkyl such as benzyl, benzhydryl, o-nitrobenzyl, p-methoxybenzyl, and p-nitrobenzyl; phthalidyl; benzyloxyalkyl having 8–10 carbon atoms such as benzyloxymethyl, and (4-nitro) benzyloxymethyl.

In addition to the esters (and thio esters) listed above, amides are also embraced by the present invention i.e., wherein $X'$ is the

group. Representative of such amides are those wherein $R'$ is selected from the group consisting of hydrogen and lower alkyl such as methyl and ethyl.

The most preferred —COX′R⁷ radicals of the present invention are those wherein (relative to Structure I above), $X'$ is oxygen and $R^7$ is hydrogen; loweralkyl having 1–4 carbon atoms; lower alkenyl such as 3-methylbutenyl, 4-butenyl and the like; benzyl and substituted benzyl such as p-nitrobenzyl Relative to the generic expression of the compounds of the present invention (I):

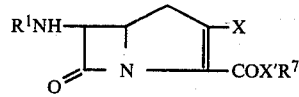

The radicals $R^1$ and/or —COX′R⁷ may be established after synthesis, rather than being established during the course of synthesis, by operating upon the 6-amino group and/or the carboxyl group. Ester embodiments involving the carboxyl group are conveniently prepared by conventional procedures known in the art; such procedures include:

1. Reaction of I with a diazoalkane such as diazomethane, phenyldiazomethane, diphenyldiazomethane, and the like in an inert solvent such as dioxane, THF, halohydrocarbons, acetonitrile, ethylacetate, and the like at a temperature of from $-78°$ C. to 25° C. for from a few minutes to 2 hours.

2. Reaction of the metallic salts (e.g., Na, Li) of the acid I with an activated alkyl halide such as methyliodide, benzylbromide, or m-phenoxybenzylbromide, p-t-butylbenzylbromide, m-phenoxybenzylbromide, and the like. Suitable reaction conditions include inert, anhydrous polar non-protic solvents such as hexamethylphosphoramide, DMF, THF, dioxane, and the like at a temperature of from $-80°$ C. to 25° C. for from a few minutes to 4 hours.

The above-recited schemes of esterification are well known in the related bicyclic β-lactam antibiotic art and indeed in all of general organic synthesis and it is to be noted that there is no undue criticality of reaction parameters in the preparation of the compounds of the present invention.

It should be noted that this N-acyl substituent, $R^1$, can either be a protecting group or an acyl radical known to be effective in the related penicillin and cephalosporin antibiotic art. When $R^1$ is a blocking group it is cleaved by well-known procedures at a convenient point in the synthesis, prior to establishment of the preferred $R^1$ by acylation procedures well-known in the bicyclic β-lactam antibiotic art. The definition of $R^1$ is more fully given below.

The compounds made available by the present invention are valuable antibiotics active against various gram-positive and gram-negative bacteria and, accordingly, find utility in human and veterinary medicine. Such sensitive bacteria representatively include: *Staphylococcus aureus, Escherichia coli, Klebsiella pneumoniae, Serratia, Salmonella typhosa, Pseudomonas* and *Bacterium proteus.* The resulting compounds may further be utilized as additives to animal feed, for preserving foodstuffs, and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example, in waterbased paints and in the white water of paper mills to inhibit the growth of harmful bacteria.

These antibiotics may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, or syrups; or may be presented as a dry product, for reconstitution with water or other suitable vehicles before use. Such liquid preparations may contain conventional additives such as suspending agents, for example, sorbitol, syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid.

Compositions for injection may be presented in unit dose form in ampules, or in multidose container. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, or throat paints, for example. For medication of the eyes or ears, the preparations may be presented as individual capsules, in liquid or semi-solid form, or may be used as drops. Topical applications may be formulated in hydrophobic or hydrophilic bases as ointments, creams, or lotions.

Also, in addition to a carrier, the instant compositions may include other ingredients such as stabilizers, binders, antioxidants, preservatives, lubricators, suspending agents, viscosity agents or flavoring agents and the like. In addition, there may also be included in the compositions other active ingredients to provide a broader spectrum of antibiotic activity.

For veterinary medicine the composition may, for example, be formulated as an intramammary preparation in either long or quick-release bases.

The dosage to be administered depends to a large extent upon the general health and weight of the subject being treated, and the route and frequency of administration—the parenteral route being preferred for generalized infections and the oral route for intestinal infections. In general, a daily oral dosage consists of from about 2 to about 600 mg. of active ingredient per kg. of body weight of the subject in one or more applications per day. A preferred daily dosage for adult humans lies in the range of from about 15 to 150 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferably to employ a dosage amount in the range of from about 100 mg. to 1000 mg. In parenteral administration the unit dosage is usually the pure compound in a slightly acidified sterile water solution or in the form of a soluble powder intended for solution.

The following Examples further illustrate the process of the present invention. All temperatures are given in °C.

EXAMPLE 1

Preparation of 4-(2-acetoxyvinyl)azetidinone-2-one $$H_2C=CH-CH=CHO\underset{\underset{O}{\|}}{C}-CH_3 + O=C=N-SO_2Cl \longrightarrow$$

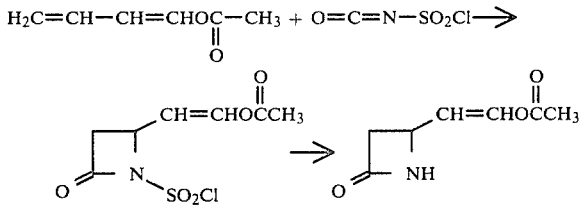

A solution of 1.0 ml distilled chlorosulfonylisocyanate (1.65 g; 11.7 mmoles) in 2.5 ml anhydrous diethyl ether is cooled under $N_2$ in a $-20°$ C. bath.

A solution of 2.5 g 1-acetoxybutadiene (22 mmoles) in 2.5 ml anhydrous ether is similarly cooled under $N_2$ in a $-20°$ C. bath.

The chlorosulfonylisocyanate solution is added dropwise to the acetoxybutadiene solution by means of a Teflon tube immersed in the CSI solution and pressurized with $N_2$. The addition takes 10 minutes. Little or no color is seen and the reaction is stirred at $-20°$ C. for 0.5 hour. The solution is clear and has a light yellow color.

A solution of 2 g sodium sulfite and 5 g $K_2HPO_4$ in 20 ml $H_2O$ is prepared during the above 0.5 hour reaction time and is cooled in an ice bath; 20 ml of ether is added and the mixture is vigorously stirred in an ice bath. At the end of the 30 minute reaction time, the reaction mixture is transferred, again using $N_2$ pressure and the Teflon tube, from the reaction flask which is maintained in the $-20°$ C. bath, to the vigorously stirred hydrolysis mixture. Rapid dropwise addition is completed in 5 minutes. The hydrolysis is allowed to continue for 5 additional minutes. The hydrolysis mix has a pH of 6–8, preferably pH 8.

The phases are separated, leaving a yellowish orange gum with the aqueous phase. The ether phase is dried directly with $MgSO_4$. The aqueous/gum phase is extracted three more times with 50 ml portions of ether, each being added to the initial ether/$MgSO_4$.

The dried extracts are filtered and concentrated under a $N_2$ stream to 5 ml; a portion of the product is crystalline at this stage.

A column of 10 g Baker silica gel, packed in ether is prepared, and the ether concentrate is applied to the top and run in. The flask/solids are rinsed three times with 2 ml ether, each being pipetted off and run into the column. Elution is then begun with ether. The first 25 ml is primarily void volume. The next five 10 ml fractions are collected followed by three 50 ml fractions, and all are reduced in volume under a N₂ stream. The product crystallizes from fractions 4–6, with traces in 3 and 7. Fractions 1–3 contain a yellowish sharp-smelling material which resinifies on standing. Yield: 100 mg as a mixture of the cis and trans isomers.

EXAMPLE 2

Preparation of 4-(2-Acetoxyethyl)-2-Azetidinone

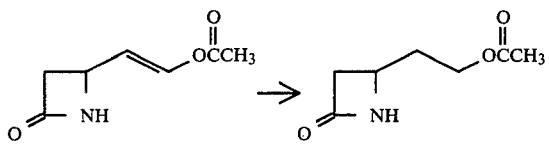

A solution of 4-(2-acetoxyvinyl)-2-azetidinone (10.0 g, 0.065 mole) in 200 ml ethyl acetate containing 100 mg of 10% Pd/C is hydrogenated on a Parr shaker at 25° C. under 40 psi hydrogen for 15 minutes. The mixture is filtered through a bed of Supercel and washed with additional ethyl acetate. The combined filtrate is evaporated in vacuo to give 4-(2-acetoxyethyl)-2-azetidinone (10.0 g) as a crystalline solid. Recrystallization from ether affords white crystals: M.P. 44-7°; ir (CHCl₃)μ5.66, 5.74; nmr (CDCl₃)τ3.44 (broad s, 1, NH), 5.82 (m, 2, C$\underline{H}_2$OCOCH₃), 6.29 (m, 1, C-4H), 6.87 (½ AB pattern further split in four by C-4H and NH, 1, $J_{gem}$=12.8 Hz, J=4.5H $J_{NH}$=1.9 Hz, 7.38 (½ AB pattern further split in four by C-4H and NH, 1, $J_{gem}$=12.8 Hz, J=2.3 Hz, $J_{NH}$=1.0 Hz), 7.93 and 8.02 (s on m, total 5, OCOC$\underline{H}_3$, and C$\underline{H}_2$CH₂OCOCH₃, respectively).

EXAMPLE 3

Preparation of 4-(2-Hydroxyethyl)-2-Azetidinone

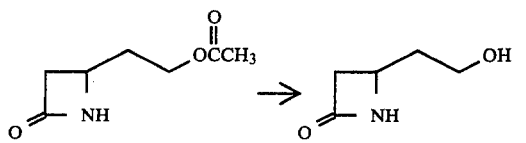

Under nitrogen at 0°, a solution of 4-(2-acetoxyethyl)-2-azetidinone (2.24 g, 0.014 mole) in 25 ml anhydrous methanol is treated with a solution of sodium methoxide (77 mg, 1.4 mmoles) in 5 ml anhydrous methanol. After stirring for 1 hour, the solution is neutralized with glacial acetic acid. Removal of the methanol in vacuo gives crude 4-(2-hydroxyethyl)-2-azetidinone as an oil. The product is purified by chromatography on silica gel eluting with 10% MeOH/CHCl₃ to give 1.55 g of the alcohol: m.p. 50°; ir (CHCl₃)μ5.67; nmr (CDCl₃)τ3.20 (broad, s, 1, NH), 6.24 and 6.28 (m on t, total 3, C-4H and CH₂OH respectively), 6.90 (broad s on ½ AB pattern further split in four by C-4H and NH, total 2, OH and C-3H respectively, $J_{gem}$=13.0 Hz, $J_{vic}$=4.2 Hz, $J_{NH}$=1.6 Hz), 7.42 (½ AB pattern further split in four by C-4H and NH, 1, C-3H, $J_{gem}$=13.0 Hz, $J_{vic}$=2.2 Hz, $J_{NH}$=1.1 Hz), 8.16 (m, 2, C$\underline{H}_2$CH₂OH).

EXAMPLE 4

Preparation of 8-oxo-2,2-dimethyl-3-oxa-1-azabicyclo[4.2.0]octane

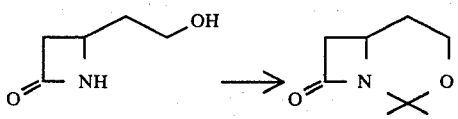

A solution of 4-(2-hydroxyethyl)-2-azetidinone (1.87 g, 0.016 mole) and 2,2-dimethoxypropane (1.69 g, 0.016 mole) in 25 ml anhydrous methylene chloride is treated with boron trifluoride etherate (0.201 ml, 0.002 mole) at 25° C. The resulting solution is stirred for ten minutes. Removal of the solvent under reduced pressure gives an oil (2.5 g). Chromatography of the crude product on silica gel using 2:1 ethyl acetate/benzene as eluting solvent gives 8-oxo-2,2-dimethyl-3-oxa-1-azabicyclo[4.2.0]octane (1.59 g) as a crystalline solid. Recrystallization from ether/hexane gives product of m.p. 60-1°.
ir (CHCl₃)μ: 5.73 (β-lactam).
nmr (CDCl₃)τ: 6.02-6.28, m, 2H, C-4 methylene, 6.22-6.62, m, 1H, C-6 methine, 6.90, dd, 1H, $J_{7,7}$=14 Hz, $J_{6,7}$=4.5 Hz, C-7 proton cis to C-6H, 7.47, dd, 1H, $J_{7,7}$=14 Hz, $J_{6,7}$=2 Hz, C-7 proton trans to C-6H, 7.82-8.68, m, 2H, C-5 methylene, 8.23, s, 3H  ⎫
            ⎬ C-2 methyls
8.57, s, 3H  ⎭

EXAMPLE 5

Preparation of 7-azido-8-oxo-2,2-dimethyl-3-oxa-1-azabicyclo[4.2.0]octane

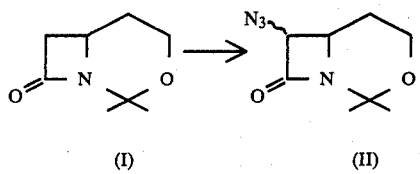

A solution of 1.54 ml (11 mmoles) of diisopropylamine in 30 ml of dry THF is cooled to −78° C. in dry-ice/acetone bath; 6.11 ml (11 mmoles) of 1.8 M methyllithium is added dropwise under nitrogen. The resulting solution is stirred at the same temperature for 1 hour; 1.55 g (10 mmol) of the bicyclic azetidinone I in 10 ml of dry THF is added dropwise. The mixture is stirred for 1 hr at −78° C. Then 2.17 g (11 mmoles) of tosylazide in 5 ml of dry THF is added dropwise. The resulting mixture is warmed to −50° C. and kept for 1.5 hrs at that temperature; 2.54 ml (20 mmol) of trimethylchlorosilane is added and the mixture is heated at reflux for 6 hrs. The reaction mixture is cooled and the solid is filtered off and washed with 2×25 ml of ether. The filtrate is concentrated. The residue is taken up in 100 ml of water and extracted with 3×25 ml of methylene chloride. The combined extracts are dried over anhydrous MgSO₄ and concentrated to give a glue which is chromatographed on silica gel (eluant 50:50 ethylacetate:cyclohexane) to give the desired 7-azido-8- oxo-2,2-dimethyl-3-oxa-1-azabicyclo[4.2.0]octane, II, as a solid (45% yield).

EXAMPLE 6

Preparation of 3-Azido-4-(2-hydroxyethyl)azetidin-2-one

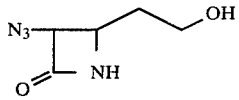

7-Azido-8-oxo-2,2-dimethyl-3-oxa-1-azabicyclo[4.2.0]-octane (0.2 mol) is dissolved in 2:1 trifluoroacetic acid —H₂O (200 ml) and the solution is kept at room temperature (25° C.) for 10 minutes. The solution is concentration under vacuum to a syrup which is taken up in ethylacetate, washed with 5% sodium bicarbonate and brine, dried with sodium sulfate, and filtered. Evaporation of the solvent provides 3-azido-4-(2-hydroxyethyl)-azetidin-2-one.

EXAMPLE 7

3-Azido-4-(2-trifluoroacetoxyethyl)-azetidin-2-one

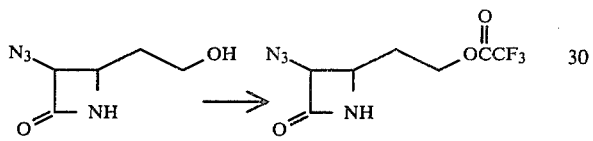

Trifluoroacetic anhydride (0.2 mol) is added dropwise to an ice-cold, stirred solution of 3-azido-4-(2-hydroxyethyl)-azetidin-2-one (0.2 mol) and pyridine (0.21 mol) in methylene chloride (200 ml). The solution is stirred for 15 more min. at room temperature (25° C.), then washed with water, dried with magnesium sulfate, and filtered. Evaporation of the methylene chloride under vacuum leaves 3-azido-4-(2-trifluoroacetoxyethyl)azetidin-2-one.

EXAMPLE 8

N-(t-Butyldimethylsilyl)-3-azido-4-(2-trifluoroacetoxyethyl)azetidin-2-one

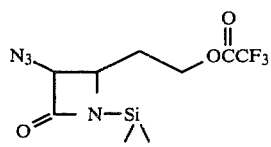

Triethylamine (0.2 mol) is added dropwise to an ice-cold stirred solution of 3-azido-4-(2-trifluoroacetoxyethyl)-azetidin-2-one (0.2 mol) and t-butyldimethylsilyl chloride (0.2 mol) in dimethylformamide (100 ml). The resulting mixture is stirred for 10 min. in the cold and for 10 min at room temperature, and then evaporated under vacuum to remove DMF. The residue is taken up in methylene chloride, washed with water and brine, dried with magnesium sulfate, and evaporated under vacuum to provide N-(t-butyldimethylsilyl)-3-azido-4-(2-trifluoroacetoxyethyl)-azetidin-2-one.

EXAMPLE 9

N-(t-Butyldimethylsilyl)-3-azido-4-(2-hydroxyethyl)-azetidin-2-one

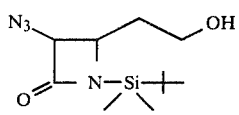

A solution of sodium methoxide (0.02 mol) in methanol (20 ml) is added to an ice-cold solution of N-(t-butyldimethylsilyl)-3-azido-4-(2-trifluoroacetoxyethyl)-azetidin-2-one (0.1 mol) in methanol (100 ml). After stirring in the cold for 10 min, the solution is treated with acetic acid (2 ml) and concentrated under vacuum. The resdue is taken up in ethyl acetate, washed with water, 5% sodium bicarbonate solution, and brine, dried, and evaporated. The residue is chromatographed on silica gel to give N-(t-butyldimethylsilyl)-3-azido-4-(2-hydroxyethyl)-azetidin-2-one.

EXAMPLE 10

N-(t-Butyldimethylsilyl)-3-azido-4-(2-oxoethyl)azetidin-2-one

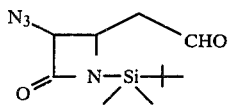

Chromium trioxide (0.06 mol) is added to a solution of pyridine (0.12 mol) in methylene chloride (150 ml) and the mixture is stirred at room temperature for 15 min. A solution of N-(t-butyldimethylsilyl)-3-azido-4-(2-hydroxyethyl)-azetidin-2-one (0.01 mol) in methylene chloride (10 ml) is then added all at once. After stirring at room temperature for 5 min, the mixture is decanted and the dark, gummy residue is washed with more methylene chloride. The combined methylene chloride supernatant is concentrated under vacuum to a residue which is taken up in ether and filtered through celite. The filtrate is washed with 5% hydrochloric acid, 5% sodium bicarbonate solution, and brine, dried with magnesium sulfate, filtered, and evaporated under vacuum to yield N-(t-butyldimethylsilyl)-3-azido-4-(2-oxoethyl)azetidin-2-one.

EXAMPLE 11

N-(t-Butyldimethylsilyl)-3-azido-4-(3-benzyloxycarbonyl-2-hydroxypropyl)-azetidin-2-one

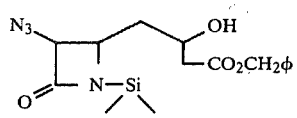

A solution of benzyl acetate (0.011 mol) in anhydrous tetrahydrofuran (5 ml) is added dropwise to solution of lithium diisopropylamide (0.011 mol) in anhydrous tetrahydrofuran (20 ml) at −78° C. After stirring 15 more min at −78° C. the reaction mixture is treated dropwise with a solution of N-(t-butyldimethylsilyl)-3-azido-4-(2-oxoethyl)-azetidin-2-one (0.01 mol) in tetrahydrofuran (10 ml). The mixture is stirred at −78° an additional 15 min and then quenched with 2.5 N hydrochloric acid (10 ml). The mixture is diluted with ethyl acetate, washed with water, 5% sodium bicarbonate solution, and brine, dried with magnesium sulfate, and evaporated under vacuum to afford N-(t-butyldimethylsilyl)-3-azido-4-(3-benzyloxycarbonyl 2-hydroxypropyl)-azetidin-2-one.

EXAMPLE 12

N-(t-Butyldimethylsilyl)-3-azido-4-(3-benzyloxycarbonyl-2-oxopropyl)azetidin-2-one

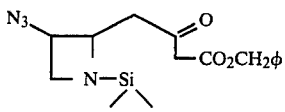

N-(t-Butyldimethylsilyl)-3-azido-4-(3-benzyloxy-2-hydroxypropyl)azetidin-2-one is oxidized by the method described in Example 10 to provide the title compound.

EXAMPLE 13

3-Azido-4-(3-benzyloxycarbonyl-2-oxopropyl)azetidin-2-one

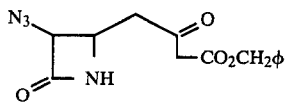

A solution of N-(t-butyldimethylsilyl)-3-azido-4-(3-benzyloxycarbonyl-2-oxopropyl)azetidin-2-one (1.0 g) in methanol (10 ml) is treated with conc. hydrochloric acid (0.1 ml) and left at room temperature for 2 hr. The solution is diluted with water and extracted with ethyl acetate. The extracts are washed with 5% sodium bicarbonate solution and brine, dried, and evaporated under vacuum. The residue is chromatographed on silica gel to give 3-azido-4-(3-benzyloxycarbonyl-2-oxopropyl)-azetidin-2-one.

EXAMPLE 14

3-Azido-4-(3-benzyloxycarbonyl-3-diazo-2-oxopropyl)-azetidin-2-one

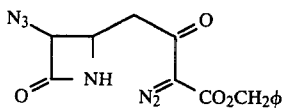

Triethylamine (15 mmol) is added to an ice-cold stirring suspension of p-carboxybenzene sulfonylazide (5 mmol) and 3-azido-4-(3-benzyloxycarbonyl-2-oxopropyl)-azetidin-2-one (5 mmol) in anhydrous acetonitrile (30 ml). The resulting mixture is stirred at room temperature for 90 mins, then diluted with ethylacetate and filtered. The filtrate is washed with water, 0.5 N sodium hydroxide, water, and brine, dried over magnesium sulfate, filtered, and evaporated under vacuum to give 3-azido-4-(3-benzyloxycarbonyl-3-diazo-2-oxopropyl)-azetidin-2-one.

EXAMPLE 15

Benzyl 6-azido-1-azabicyclo[3.2.0]heptan-3,7-dione-2-carboxylate

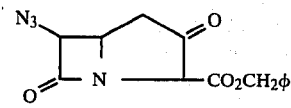

A suspension of rhodium acetate (2 mg) and 3-azido-4-(3-benzyloxycarbonyl-3-diazo-2-oxopropyl)azetidin-2-one (1 mmol) in anhydrous benzene (20 ml) is deoxygenated by bubbling nitrogen through it for 15 mins. The suspension is then stirred with heating in an oil bath at 80° C. for 30 min. After cooling to room temperature, the mixture is filtered and the filtrate is evaporated under vacuum to provide benzyl 6-azido-1-azabicyclo[3.2.0]-heptan-3,7-dione-2-carboxylate.

EXAMPLE 16

Benzyl 6-azido-3-acetoxy-1-azabicyclo[3.2.0]-hept-2-en-7-one-2-carboxylate

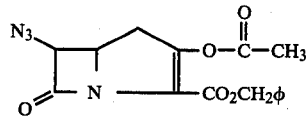

A solution of benzyl 6-azido-1-azabicyclo[3.2.0]heptan-3,7-dione-2-carboxylate (1 mmol) and acetic anhydride (10 mmol) in anhydrous pyridine (1 ml) is kept at 0°–5° C. for 3 days. The solution is concentrated under vacuum, diluted with ethyl acetate, washed with water, pH 2 buffer, 5% sodium bicarbonate solution, and brine, dried with magnesium sulfate, filtered, and evaporated under vacuum to give benzyl 6-azido-3-acetoxyl-1-azabicyclo[3.2.0]hept-2-en-7-one-2-carboxylate.

EXAMPLE 17

Benzyl 6-azido-3-methoxy-1-azabicyclo[3.2.0]hept-2-en-7-one-2-carboxylate

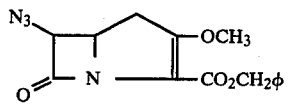

Benzyl 6-azido-1-azabicyclo[3.2.0]heptan-3,7-dione-2-carboxylate (1 mmol) is dissolved in anhydrous acetone (5 ml) and treated with powdered, anhydrous potassium carbonate (2 mmol). The resulting suspension is treated with dimethyl sulfate (1.2 mmol) and stirred vigorously at room temperature for several hours. The mixture is diluted with ethylether and filtered. The filtrate is washed with water and brine, dried and evaporated under vacuum to give benzyl 6-azido-3-methoxy-1-azabicyclo[3.2.0]hept-2-en-7-one-2-carboxylate.

EXAMPLE 18

Benzyl 6-azido-3-toluenesulfonyloxy-1-azabicyclo[3.2.0]hept-2-en-7-one-2-carboxylate

p-Toluenesulfonic anhydride (1 mmol) and triethylamine (1.2 mmol) are added to an ice-cold solution of benzyl 6-azido-1-azabicyclo[3.2.0]-heptan-3,7-dione-2-carboxylate (1 mmol) in anhydrous methylene chloride (10 ml). After stirring in the cold for 2 hr, the solution is washed with water, pH 3 phosphate buffer, and 5% sodium bicarbonate solution, dried over magnesium sulfate, filtered, and evaporated under vacuum to give benzyl 6-azido-3-toluenesulfonyloxy-1-azabicyclo[3.2.0]hept-2-en-7-one-2-carboxylate.

EXAMPLE 19

Benzyl 6-azido-3-chloro-1-azabicyclo[3.2.0]hept-2-en-7-one-2-carboxylate

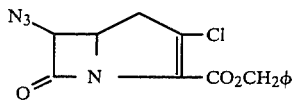

Phosphorus trichloride (1 mmol) is added to a solution of benzyl 6-azido-1-azabicyclo[3.2.0]heptan-3,7-dione-2-carboxylate (0.5 mmol) in anhydrous dimethylformamide (2.5 ml) and the mixture is left to stand at room temperature. After 5 hr, the mixture is diluted with toluene, washed with water, 1 N hydrochloric acid, 5% sodium bicarbonate solution, and brine, dried over magnesium sulfate, and filtered. Evaporation of the solvent under vacuum yields benzyl 6-azido-3-chloro-1-azabicyclo[3.2.0]-hept-2-en-7-one-2-carboxylate.

EXAMPLE 20

Benzyl 6-azido-3-(2-diethylaminoethyloxy)-1-azabicyclo[3.2.0-]hept-2-en-7-one-2-carboxylate

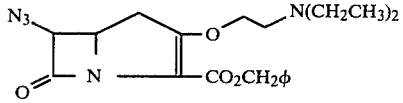

An ice-cold solution of benzyl 6-azido-1-azabicyclo[3.2.0]heptan-3,7-dione-2-carboxylate (1 mmol) in anhydrous dimethylformamide (1 ml) is added dropwise to an ice-cold mixture of potassium hydride (1 mmol) in anhydrous dimethylformamide (4 ml). After stirring for several minutes in the cold and under nitrogen, the mixture is treated with diethylaminoethyl chloride and stirred in the cold for 2 hr. The mixture is diluted with ethyl acetate, washed thoroughly with water and brine, dried over magnesium sulfate, and filtered. Evaporation of the solvent in vacuo gives benzyl 6-azido-3-(2-diethylaminoethyloxy)-1-azabicyclo[3.2.0]hept-2-en-7-one-2-carboxylate.

EXAMPLE 21

6-Amino-3-acetoxy-1-azabicyclo[3.2.0]-hept-2-en-7-one-2-carboxylic acid

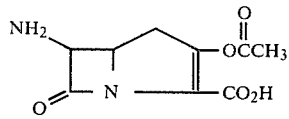

A suspension of 5% palladium on powdered charcoal (200 mg) in ethanol (5 ml) is hydrogenated at 40 psi for 30 mins. The catalyst is collected by centrifugation, washed twice with methanol, and suspended in methanol (2 ml). A solution of benzyl 6-azido-3-acetoxy-1-azabicyclo[3.2.0]hept-2-en-7-one-2-carboxylate (100 mg) in tetrahydrofuran (2 ml) is added to the catalyst suspension and the mixture is hydrogenated at 40 psi for 2 hr. The catalyst is filtered off and washed with several portions of methanol. The combined filtrate and washings is evaporated under vacuum to provide 6-amino-3-acetoxy-1-azabicyclo[3.2.0]hept-2-en-7-one-2-carboxylic acid.

EXAMPLE 22

Sodium 6-(2-thienylacetamido)-3-acetoxy-1-azabicyclo[3.2.0-]hept-2-en-7-one-2-carboxylate

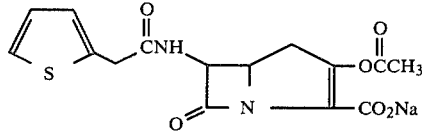

6-Amino-3-acetoxy-1-azabicyclo[3.2.0]hept-2-en-7-one-2-carboxylic acid (0.1 mmol) is dissolved in ice-cold water (2 ml) containing sodium bicarbonate (1 mmol). The solution is diluted with dioxane (1 ml) and then treated dropwise over 10 min with a solution of 2-thienylacetyl chloride (0.1 mmol) in dioxane (0.5 ml). After stirring in the cold for 15 more min, the reaction mixture is acidified to pH 7 with 1 M sulfuric acid and extracted with ether. The aqueous portion is layered with ethyl acetate and stirred vigorously with ice-bath cooling while acidifying to pH 2.5 with 1 M sulfuric acid. The ethylacetate layer is separated, washed with cold brine, and then thoroughly extracted with a cold solution of sodium bicarbonate (0.1 mmol) in water. The aqueous extract is concentrated under vacuum and lyophilized to provide sodium 6-(2-thienylacetamido)-3-acetoxy-1-azabicyclo[3.2.0]hept-2-en-7-one-2-carboxylate.

EXAMPLE 23

6-Amino-3-methoxy-1-azabicyclo[3.2.0]hept-2-en-7-one-2-carboxylic acid

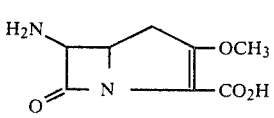

Benzyl 6-azido-3-methoxy-1-azabicyclo[3.2.0]hept-2-en-7-one-2-carboxylate is converted to the title compound as described in Example 21.

EXAMPLE 24

Sodium 6-phenoxyacetamido-3-methoxy-1-azabicyclo[3.2.0]hept-2-en-7-one-2-carboxylate

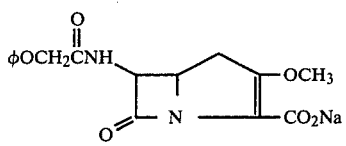

6-Amino-3-methoxy-1-azabicyclo[3.2.0]hept-2-en-7-one-2-carboxylic acid is acylated with phenoxyacetyl chloride by the procedure of Example 22 to yield the title compound.

EXAMPLE 25

Benzyl 6-amino-3-chloro-1-azabicyclo[3.2.0]hept-2-en-7-one-2-carboxylate

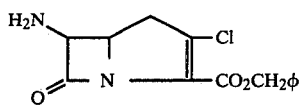

A mixture of platinum oxide (100 mg), benzyl 6-azido-3-chloro-1-azabicyclo[3.2.0]hept-2-en-7-one-2-carboxylate (80 mg), and ethyl acetate (2 ml) is hydrogenated on a Paar shaker for 30 mins at 45 psi. The resulting mixture is filtered through a pad of silica gel G which is washed with additional ethyl acetate. The filtrate is washed with water and brine, dried with magnesium sulfate, and evaporated under vacuum to afford benzyl 6-amino-3-chloro-1-azabicyclo[3.2.0]hept-2-en-7-one-2-carboxylate.

EXAMPLE 26

Benzyl 6-(α-azido-phenylacetamido)-3-chloro-1-azabicyclo[3.2.0]hept-2-en-7-one-2-carboxylate

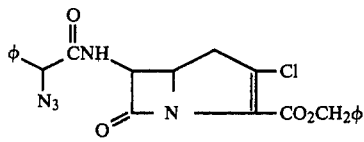

To an ice-cold solution of benzyl 6-amino-3-chloro-1-azabicyclo[3.2.0]hept-2-en-7-one-2-carboxylate (0.2 mmol) in methylene chloride (2 ml) containing anhydrous pyridine (0.1 ml) is added α-azidophenylacetyl chloride (0.2 mmol). After stirring in the cold for 60 mins, the solution is washed with water, pH 3 phosphate buffer, 5% sodium bicarbonate solution and brine, dried with magnesium sulfate, filtered, and evaporated under vacuum to give benzyl 6-(α-azido-phenylacetamido)-3-chloro-1-azabicyclo[3.2.0]hept-2-en-7-one-2-carboxylate.

EXAMPLE 27

6-(α-Amino-phenylacetamido)-3-chloro-1-azabicyclo[3.2.0]hept-2-en-7-one-2-carboxylic acid

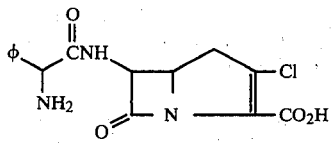

A mixture of 10% palladium on charcoal (50 mg) and benzyl 6-(α-azido-phenylacetamido)-3-chloro-1-azabicyclo[3.2.0]hept-2-en-7-one-2-carboxylate (50 mg) in 1:1 water-dioxane (2 ml) is hydrogenated at 40 psi for 60 mins. The catalyst is filtered off and washed thoroughly with water. The combined aqueous filtrate and washings are extracted with ethyl acetate, evaporated under vacuum to remove dissolved organic solvents, and lyophilized to yield 6-(α-amino-phenylacetamido)-3-chloro-1-azabicyclo[3.2.0]hept-2-en-7-one-2-carboxylic acid.

EXAMPLE 28

6-Amino-3-(2-diethylaminoethyloxy)-1-azabicyclo[3.2.0]hept-2-en-7-one-2-carboxylate acid

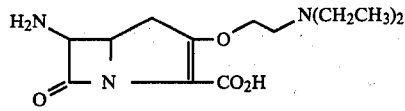

A solution of benzyl 6-azido-3-(2-diethylaminoethyloxy)-1-azabicyclo[3.2.0]hept-2-en-7-one-2-carboxylate (100 mg) in dioxane (2 ml) is diluted with water (1 ml) and treated with 10% palladium on charcoal (100 mg). The resulting suspension is hydrogenated at 40 psi for 30 min. The mixture is filtered and the catalyst washed with several portions of water. The combined filtrate plus washings is concentrated under vacuum to remove most of the dioxane and then lyophilized to afford 6-amino-3-(2-diethylaminoethyloxy)-1-azabicyclo[3.2.0]hept-2-en-7-one-2-carboxylic acid.

EXAMPLE 29

6-Phenylacetamido-3-(2-diethylaminoethyloxy)-1-azabicyclo[3.2.0]hept-2-en-7-one-2-carboxylic acid

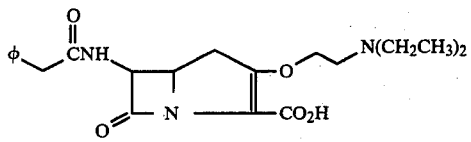

An ice-cold, stirring solution of 6-amino-3-(2-diethylaminoethyloxy)-1-azabicyclo[3.2.0]hept-2-en-7-one-2-carboxylic acid (0.1 mmol) and sodium bicarbonate (0.5 mmol) in water (2.5 ml) and dioxane (2 ml) is treated dropwise with a solution of phenylacetyl chloride (0.12 mmol) in dioxane (0.5 ml). After stirring 30 mins in the cold, the mixture is acidified to pH 7 with 0.1 N hydrochloric acid, extracted with ethylacetate, and concentrated under pressure to ca. 1 ml. The concentrate is charged onto a Dowex 50-X4 (sodium form) column which is eluted with water. The desired fractions are concentrated under vacuum and lyophilized to afford 6-phenylacetamido-3-(2-diethylaminoethyloxy)1-azabicyclo[3.2.0]hept-2-en-7-one-2-carboxylic acid.

EXAMPLE 30

Preparation of Pharmaceutical compositions

One such unit dosage form is made by mixing phenylacetamido-3-(2-diethylaminoethyloxy)-1-azabicyclo[3.2.0]hept-2-en-7-one-2-carboxylic acid (120 mg) with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules and should it be necessary to mix more than 145 mg of ingredients together, larger capsules such as compressed tablets and pills can also be prepared. The following examples are illustrative of the preparation of pharmaceutical formulations:

| TABLET | PER TABLET |
|---|---|
| 6-phenylacetamido-3-(2-diethylaminoethyloxy)-1-azabicyclo[3.2.0]hept-2-en-7-one-2-carboxylic acid | 125 mg. |
| Cornstarch, U.S.P. | 6 mg. |
| Dicalcium Phosphate | 192 mg. |
| Lactose, U.S.P. | 190 mg. |
| Magnesium Stearate | Balance/800 mg. |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| | PER TABLET |
|---|---|
| PARENTERAL SOLUTION Ampoule: | |
| 6-phenylacetamido-3-(2-diethylaminoethyloxy)-1-azabicyclo[3.2.0]hept-2-en-7-one-2-carboxylic acid | 500 mg. |
| Diluent: Sterile Water for Injection | 2 cc. |
| OPTHALMIC SOLUTION | |
| 6-phenylacetamido-3-(2-diethylaminoethyloxy)-1-azabicyclo[3.2.0]hept-2-en-7-one-2-carboxylic acid | 100 mg. |
| Hydroxypropylmethyl cellulose | 5 mg. |
| Sterile Water | to 1 ml. |
| OTIC SOLUTION | |
| 6-phenylacetamido-3-(2-diethylaminoethyloxy)-1-azabicyclo[3.2.0]hept-2-en-7-one-2-carboxylic acid | 100 mg. |
| Benzalkonium chloride | 0.1 mg. |
| Sterile Water | to 1 ml. |
| TOPICAL OINTMENT | |
| 6-phenylacetamido-3-(2-diethylaminoethyloxy)-1-azabicylco[3.2.0]hept-2-en-7-one-2-carboxylic acid | 100 mg. |
| Polyethylene Glycol 4000 U.S.P. | 400 mg. |
| Polyethylene Glycol 400 U.S.P. | 1.0 gram. |

The active ingredient in the above formulation may be administered alone or in combination with other biologically active ingredients as, for example, with other antibacterial agents such as lincomycin, a penicillin, streptomycin, novobiocin, gentamicin, neomycin, colistin and kanamycin or with other therapeutic agents such as probenecid.

What is claimed is:

1. The compound of the formula:

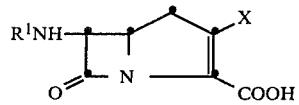

or pharmaceutically acceptable salts thereof; wherein X is chloro, acetyl, methoxy,

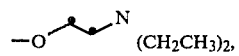

or oxo, with the proviso that when X is oxo, 2–3 bond is saturated; and $R^1$ is

wherein R" is benzyl, p-hydroxybenzyl, 4-amino-4-carboxybutyl, methyl, cyanomethyl, 2-pentenyl, n-amyl, n-heptyl, ethyl, 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4-N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)-4-isoxazolyl, 4-guanidinomethylphenyl, 4-guanidinomethylbenzyl, 4-guanidinobenzyl, 4-guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl)vinyl, phenyl, o-methoxyphenyl, o-chlorophenyl, 1-phenylphenyl, p-aminomethylbenzyl, 1-(5-cyanotriazolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl)methyl, 2- or 3-(methoxythienyl)methyl, 2- or 3-(4-chlorothienyl)methyl, 2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, tetrazolylmethyl benzamidinomethyl and cyclohexylamidinomethyl.

2. The compound of the formula:

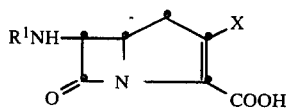

or pharmaceutically acceptable salts thereof; wherein X is chloro, acetyl, methoxy,

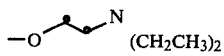

or oxo, with the proviso that when X is oxo, the 2–3 bond is saturated; and $R^1$ is selected from the group consisting of: phenylacetyl, phenoxyacetyl, 3-bromophenylacetyl, p-aminomethylphenylacetyl, 4-carboxymethylphenylacetyl, 4-carboxamidomethylphenylacetyl, 2-furylacetyl, 5-nitrofurylacetyl, 3-furylacetyl, 2-thienylacetyl, 5-chlorothienylacetyl, 5-methoxythienylacetyl, α-guanidino-2-thienylacetyl, 3-thienylacetyl, 4-methylthienylacetyl, 3-isothiazolylacetyl, 4-methoxyisothiazolylacetyl, 4-isothiazolylacetyl, 3-methylisothiazolylacetyl, 5-isothiazolylacetyl, 3-chloroisothiazolylacetyl, 3-methyl-1,2,5-oxadiazolylacetyl, 1,2,5-thiadiazolyl-4-acetyl, 3-methyl-1,2,5-thiadiazolyl-4-acetyl, 3-chloro-1,2,5-thiadiazolyl-4-acetyl, 3-methoxy-1,2,5-thiadiazolyl-4-acetyl, phenylthioacetyl, 4-pyridylthioacetyl, cyanoacetyl, tetrazolylacetyl, α-fluorophenylacetyl, D-phenylglycyl, 3-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-sulfaminophenylacetyl, α-hydroxyphenylacetyl, α-tetrazolylphenylacetyl and α-sulfophenylacetyl.

* * * * *